United States Patent
Gleich

(10) Patent No.: US 9,808,173 B2
(45) Date of Patent: Nov. 7, 2017

(54) METHOD FOR THE SPATIALLY RESOLVED DETERMINATION OF PHYSCIAL, CHEMICAL AND/OR BIOLOGICAL PROPERTIES OR STATE VARIABLES

(75) Inventor: Bernhard Gleich, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 3748 days.

(21) Appl. No.: 10/552,818

(22) PCT Filed: Apr. 15, 2004

(86) PCT No.: PCT/IB2004/050447
§ 371 (c)(1),
(2), (4) Date: Oct. 11, 2005

(87) PCT Pub. No.: WO2004/091396
PCT Pub. Date: Oct. 28, 2004

(65) Prior Publication Data
US 2006/0210987 A1    Sep. 21, 2006

(30) Foreign Application Priority Data
Apr. 15, 2003 (EP) ..................................... 03101022

(51) Int. Cl.
| | |
|---|---|
| G01N 33/48 | (2006.01) |
| A61B 5/05 | (2006.01) |
| G06F 11/07 | (2006.01) |
| A61B 5/06 | (2006.01) |
| A61K 49/18 | (2006.01) |
| G06G 7/58 | (2006.01) |

(52) U.S. Cl.
CPC .............. *A61B 5/0515* (2013.01); *A61B 5/06* (2013.01); *A61K 49/1818* (2013.01); *G06F 11/0736* (2013.01)

(58) Field of Classification Search
CPC ............................. G01N 19/32; G01N 19/322
See application file for complete search history.

(56) References Cited

U.S. PATENT DOCUMENTS

| | | | |
|---|---|---|---|
| 4,136,683 A | 1/1979 | Gordon | |
| 4,537,861 A | 8/1985 | Elings | |
| 4,764,445 A * | 8/1988 | Miskinis et al. | 430/111.33 |
| 5,543,174 A * | 8/1996 | Rutz | 427/213 |
| 5,679,323 A | 10/1997 | Menz | |
| 6,082,366 A | 7/2000 | Andra et al. | |
| 7,778,681 B2 | 8/2010 | Gleich | |
| 2002/0136693 A1 | 9/2002 | Gries | |

FOREIGN PATENT DOCUMENTS

| | | |
|---|---|---|
| EP | 0095124 A1 | 5/1983 |
| EP | 1304542 A2 | 4/2003 |
| WO | 199952505 A1 | 10/1999 |

OTHER PUBLICATIONS

Heldemann et al. "A Brief review of parallel magnetic resonance imaging" Eur Radiol (2003) vol. 13, pp. 2323-2337.*
Wasterby et al. "Anisotropic Water Diffusion in Macroscopically Oriented Lipid Bilayers by Pulsed Magnetic Field Gradient NMR" Journal of Magnetic Resonance (2002) vol. 157, pp. 156-159.*
Collin et al. "NMR Characterization of a kissing complex formed between the TAR RNA element of HIV-I and a DNA aptamer", Nucleic acids research (2000), vol. 23, pp. 3382-3391.*
Pitto et al. "Gradient-Tailored excitation for single quantum NMR Spectroscopy of an aqueous solution" Journal of Biomolecular NMR (1992) pp. 661-665.*
Evans "Biomolecular NMR Spectroscopy" Oxford Press. 1995, pp. 5-9, 11, 66, 71, 75, 76, and title page.*
ISR: PCT/IB04/050447.
Written Opinion: PCT/IB04/050447.
Hinshaw, Waldo S. "Image Formation by Nuclear Magnetic Resonance: The Sensitive-Point Method", Journal of Applied Physics, vol. 47, No. 8, Aug. 1978, pp. 3709-3721.

* cited by examiner

*Primary Examiner* — Eric S Dejong

(57) ABSTRACT

Method for the spatially resolved determination of physical, chemical and/or biological properties or state variables and/or the change therein in an examination area of an examination object by determining the change in the spatial distribution and/or the mobility, particularly the mobility in rotation, of magnetic particles in this examination area or in parts thereof as a function of the effect of physical, chemical and/or biological influencing variables on at least a part-area and/or in the physical, chemical and/or biological conditions in at least a part-area of the examination area, by means of the following steps: a) introducing covered and/or coated magnetic particles with at least one solid, viscous and/or liquid shell or coating into at least part of the examination area and/or introducing magnetic particles into at least part of the examination area and/or covering and/or coating at least some of these particles in the examination area, b) generating a magnetic field with a spatial profile of the magnetic field strength such that there is produced in the examination area a first part-area having a low magnetic field strength and a second part-area having a higher magnetic field strength, 15 c) changing the, in particular relative, spatial position of the two part-areas in the examination area or changing the magnetic field strength in the first part-area so that the magnetization of the particles is locally changed, d) detecting signals that depend on the magnetization in the examination area that is influenced by this change, and e) evaluating the signals so as to obtain information about the change in the spatial distribution and/or mobility of the magnetic particles in the examination area. The invention also relates to functionalized magnetic particle compositions and magnetic particle compositions suitable for use in the above method. The invention further also relates to an apparatus for the measurement of state variables in the examination area.

24 Claims, No Drawings

METHOD FOR THE SPATIALLY RESOLVED DETERMINATION OF PHYSCIAL, CHEMICAL AND/OR BIOLOGICAL PROPERTIES OR STATE VARIABLES

The present invention relates to a method for the spatially resolved determination of physical, chemical and/or biological properties or state variables and/or the change therein in an examination area of an examination object. Further, the invention also relates to functionalised magnetic particle compositions for use in the method according to the invention. The invention further also relates to an apparatus for the measurement of state variables in the examination area.

For determining physical, chemical and biological state variables of any kind there are a large number of direct and indirect measurement methods available to the person skilled in the art, depending on the desired aim and the object that is to be examined. Often those measurement methods which can be used to determine state parameters in media which are not directly accessible to a measurement instrument or a measurement probe are of particular interest. Suitable examples of indirect parameter determination include the monitoring of reaction parameters such as temperature and the progress of the reaction in chemical preparation methods by means of optical methods or the determining of the quality of material parts, for example the existence of cracks, by means of ultrasound. Particularly when examining living tissue, it is often necessary to use indirect measurement methods to determine for example temperature, pH or the concentration of specific substances. However, such indirect measurement methods are often more complex and entail greater measurement errors than direct determination methods. Therefore, for many preparation methods or products there is an increasing need for ways of being able to determine in a very precise manner the parameters that are to be examined, in a non-destructive and indirect manner. Those measurement methods which can be used to determine in a targeted manner information about locally closely delimited regions of an examination object are of particular significance.

One method for the non-invasive determination of chemical and physical states within an animal or human body can be found for example in EP 0 95 124 A. According to said document, the temperature and pH within selected volume segments in an examination area can be determined or found from the parameters of a measured nuclear resonance spectrum by using magnetic resonance spectroscopy with a homogeneous constant magnetic field and a high frequency magnetic field.

In one refinement of the method according to EP 0 95 124 A, besides a homogeneous constant magnetic field three orthogonally running gradient fields are generated which are modulated asynchronously in terms of time, as a result of which a local magnetic resonance signal is detected only at the intersection of the three planes of the gradient fields. This embodiment is described in the literature as the "sensitive point" method (cf. Hinshaw, J. Appl. Phys. 47 (1976), pages 3709 to 3721). According to EP 0 95 124 A it is furthermore possible to obtain information about the temperature and pH in living objects by superposing a gradient field on a homogeneous magnetic field such that only a narrowly delimited volume in the region of the measurement point that is to be examined has a high homogeneity and all surrounding regions have a considerably inhomogeneity. This method is known in the literature as the "FONAR" method (cf. Damadian, Physiol. Chem. Phys. 8 (1976), pages 61 to 65). One disadvantage of the measurement method proposed in EP 0 95 124 is that it is not readily possible to move the locally delimited examination area or allow it to migrate in order for example to be able to obtain reliable information about a larger coherent examination area or in order to be able to monitor at the same time local changes in the examination object. Although it has been possible in recent years to considerably increase the measurement speed by improving magnetic resonance imaging (MRI) methods, the determination of parameters such as temperature, pressure and pH is still too slow and inaccurate for many applications.

DE 37 51 918 T2 describes a method for obtaining an in vivo image of an animal or human organ or tissue with the aid of nuclear spin resonance technology, in which an image-improving dose of a nuclear spin tomography contrast agent is used in the form of a superparamagnetic fluid that is to be prepared in a specific manner. The magnetic properties of the examined tissue are said to be influenced by the magnetic contrast agent such that the irradiated protons exhibit an improved relaxation behavior. Superparamagnetic and ferromagnetic substances allow the magnetic resonance image to appear darker by reducing $T_2$. Suitable contrast agents for nuclear spin tomography nevertheless often require an extremely stable solution in order to be able to effectively increase the sensitivity of the nuclear resonance measurement. However, the stability of suitable aqueous fluids of superparamagnetic iron oxides is often considerably restricted by clumping together as a result of magnetic attraction forces between the particles. DE 37 51 918 T2 proposes a four-stage method for preparing a stable superparamagnetic fluid from divalent and trivalent metal salts. This method is very time-consuming and cost-intensive and therefore cannot necessarily be used for standard examinations. Although the magnetic particles obtained with this method may help to increase the anatomical and physiological contrast, they are often not suitable for making parameters such as temperature and pH more accurately and rapidly detectable using MRI technology. In addition, nuclear spin tomography requires the use of very strong magnetic fields having a high homogeneity. For this, use is usually made of supraconductive coils using cooling by means of liquid helium. The method of nuclear spin tomography is consequently always associated with a high outlay on apparatus.

Nuclear spin resonance measurements, as described by Perez et al. (J. Am. Chem. Soc., 2002, 124 (12), pages 2856 and 2867), are likewise used to detect DNA interactions. Here, use is made of the fact that DNA or oligonucleotide sequences bound to magnetic particles hybridize with complementary DNA. If the complementary DNA is also bound to a magnetic particle, this may result in a stable cluster formation with the result that the $T_2$ relaxation times of water molecules adjacent to hydrogen nuclei decrease. This change can be made visible by means of nuclear spin tomography.

It is therefore an object of the present invention to make available a method of determining in particular locally delimited state variables in an examination area in a manner that is simple in terms of apparatus and hence cost-effective and also reproducible and accurate, which method also no longer has the disadvantages of the measurement methods of the prior art. Furthermore, it is an object of the present invention to provide a method for the locally delimited determination of physical, chemical or biological state variables or changes in state variables which can be used for the in situ determination of these state variables and allows the examination of materials and also of living matter.

Accordingly, there has been found a method for the spatially resolved determination of physical, chemical and/or biological properties or state variables, particularly substance concentrations, temperature, pH and/or physical fields, and/or the change in such physical, chemical and/or biological properties or state variables in an examination area of an examination object by determining the change in the spatial distribution and/or the mobility, particularly the mobility in rotation, of magnetic particles in this examination area or in parts thereof as a function of the effect of physical, chemical and/or biological influencing variables on at least a part-area and/or in the physical, chemical and/or biological conditions in at least a part-area of the examination area, by means of the following steps:

a) introducing at least partially covered and/or coated magnetic particles with at least one solid, viscous and/or liquid shell or coating into at least part of the examination area and/or introducing magnetic particles into at least part of the examination area and/or covering and/or coating at least some of these particles in the examination area, b) generating a magnetic field with a spatial profile of the magnetic field strength such that there is produced in the examination area a first part-area having a low magnetic field strength and a second part-area having a higher magnetic field strength, c) changing the, in particular relative, spatial position of the two part-areas in the examination area or changing the magnetic field strength in the first part-area so that the magnetization of the particles is locally changed, d) detecting signals that depend on the magnetization in the examination area that is influenced by this change, and e) evaluating the signals so as to obtain information about the change in the spatial distribution and/or mobility of the magnetic particles in the examination area.

In a preferred embodiment, step b) takes place before step a) or steps a) and b) are carried out essentially at the same time and/or steps c) to e) are repeated at least once.

In principle, any desired object can be examined using the method according to the invention, regardless of the composition, consistency, shape or size, as long as the particles can be introduced into and are accepted by the environment. By way of example, liquid, viscous and solid examination objects can readily be analyzed by means of the method according to the invention.

According to a preferred refinement of the method according to the invention it may be provided that the examination object is a polymer material, in particular a thermoplastic polymer or a polymer blend, a polymer melt, a microorganism, a plant, a plant part, a living thing or a part of a living thing.

It may be provided that the degree of mobility of the magnetic particles in the examination area is determined continuously or at intervals and is correlated with a state variable or property of the examination area, in particular a temperature, a concentration and/or a viscosity. The mobility of magnetic particles within a shell may be restricted for example in terms of the ability of these particles to undergo (Brown's) rotation. The ability of magnetic particles to be aligned by means of rotation upon application of a magnetic field often depends on the covering or on the viscosity of the covering and/or on the degree of resolution or imaging of the shell. Determining the rotation mobility of the magnetic particles therefore makes it possible to be able to draw conclusions about the surroundings of the magnetic particles or about state conditions in the examination area.

One development of the method according to the invention likewise provides that the degree of mobility of the magnetic particles in a polymer melt that is forming or curing is determined continuously or at intervals and is correlated with the degree of curing or the degree of melting of a polymer material, in particular of a thermoplastic polymer.

Particularly good results are obtained when at least some of the magnetic particles have anisotropic properties.

The method according to the invention makes use of the fact that magnetic particles which are not saturated may be influenced by an external magnetic field, with it being possible for the reaction thereof to the external magnetic field to be detected. In this way it is possible to draw conclusions about the environment in which the magnetic particles are present. In the case of a particularly anisotropic magnetic particle, a reaction to or an interaction with an applied external field, that is to say a magnetization reversal, takes place particularly easily when this particle is not prevented by external, e.g. mechanical, influences from aligning in the direction of the field lines of the external magnetic field. Since the behavior of the magnetic particles in the examination area depends considerably on their immediate surroundings, it is possible to precisely determine for example when this magnetic particle changes its state or gains or loses mobility. In the method according to the invention, the immobilization of the magnetic particles is obtained by means of coatings or coverings. These often prevent a magnetization reversal of the particles for as long as they are not at least partially degraded or dissolved.

The method according to the invention makes substantial use of an arrangement as described in the unpublished German patent application having the number 101 51 778.5. Reference is hereby also made to the aforementioned patent application in respect of preferred embodiments of this arrangement.

A spatially inhomogeneous magnetic field is generated in the examination area by means of the arrangement used according to the invention. In the first part-area the magnetic field is so weak that the magnetization of the particles differs to a greater or lesser extent from the external magnetic field, that is to say is not saturated. This first part-area is preferably a spatially coherent area; it may also be a punctiform area or else a line or a flat area. In the second part-area (i.e. in the rest of the examination area outside the first part) the magnetic field is strong enough to keep the particles in a state of saturation. The magnetization is saturated when the magnetization of virtually all particles is aligned in approximately the direction of the external magnetic field, so that the magnetization there increases much less with a further increase in the magnetic field than in the first part-area given a corresponding increase in the magnetic field.

By changing the position of the two part-areas within the examination area, the (overall) magnetization in the examination area changes. If, therefore, the magnetization in the examination area or physical parameters influenced thereby is/are measured, information about the spatial distribution of the magnetic particles in the examination area can then be derived therefrom.

In order to change the spatial position of the two part-areas in the examination area or to change the magnetic field strength in the first part area, for example, a magnetic field that can be changed locally and/or temporally can be generated. It may also be provided that the signals induced in at least one coil by the temporal change in the magnetization in the examination area are received and evaluated in order to obtain information about the spatial distribution of the magnetic particles in the examination area Signals that are as great as possible can be obtained by the spatial position of the two part-areas changing as rapidly as possible. A coil which is used to generate a magnetic field in the examination area can be used to detect the signals. However, at least one special coil is preferably used to receive signals.

The change in the spatial position of the part-areas may also take place, for example, by means of a temporally changing magnetic field. In this case a likewise periodic signal is induced in a coil. However, this signal may be difficult to receive since the signals generated in the examination area and the temporally changing magnetic field are active at the same time; it is therefore not readily possible to distinguish between the signals induced by the magnetic field and the signals induced by changing the magnetization in the examination area. However, this can be avoided by a temporally changing magnetic field acting on the examination area in a first frequency band and, from the signal received in the coil, a second frequency band which contains higher frequency components than the first frequency band being evaluated so as to obtain information about the spatial distribution of the magnetic particles. This makes use of the fact that the frequency components of the second frequency band can occur only by virtue of a change in the magnetization in the examination area as a result of the non-linearity of the magnetization characteristic. If the temporally changing magnetic field has a sinusoidal periodic profile, the first frequency band consists only of a single frequency component—the sinusoidal fundamental component By contrast, besides this fundamental component the second frequency band also contains higher harmonics (so-called upper harmonics) of the sinusoidal fundamental component, which can be used for the evaluation.

One preferred arrangement for the method according to the invention is characterized in that the means for generating the magnetic field comprise a gradient coil arrangement for generating a magnetic gradient field which in the first part-area of the examination area reverses its direction and has a zero crossing. This magnetic field is—if the gradient coil arrangement comprises e.g. two identical windings which are arranged on either side of the examination area but which are flowed through by opposite currents (Maxwell coil)—zero at a point on the winding axis and increases virtually linearly on either side of this point with opposite polarity. Only in the case of particles which are located in the region around this field zero point is the magnetization not saturated. In respect of particles outside this area the magnetization is in a state of saturation.

An arrangement may be provided with means for generating a temporally changing magnetic field that is superposed on the magnetic gradient field for the purpose of moving the two part-areas in the examination area. The area generated by the gradient coil arrangement is in this case moved around the field zero point, i.e. the first part-area, within the examination area by the temporally changing magnetic field. Given a suitable temporal profile and orientation of this magnetic field it is possible in this way for the field zero point to pass through the entire examination area.

The change in magnetization that is associated with the movement of the field zero point may be received by means of an appropriate coil arrangement. The coil used to receive the signals generated in the examination area may be a coil which is already used to generate the magnetic field in the examination area. However, there are also advantages to using at least one special coil for receiving, since this can be decoupled from the coil arrangement that generates a temporally changing magnetic field. Moreover, an improved signal-to-noise ratio can be achieved with one coil—but all the more so with a number of coils.

The amplitude of the signals induced in the coil arrangement is greater the quicker the position of the field zero point in the examination area changes, that is to say the quicker the temporally changing magnetic field superposed on the magnetic gradient field changes. However, it is technically difficult to generate on the one hand a temporally changing magnetic field whose amplitude is sufficient to move the field zero point to the point of the examination area and whose rate of change is sufficiently high to generate signals having a sufficient amplitude. Particularly suitable for this are those arrangements which have means for generating a first and at least a second magnetic field that are superposed on the magnetic gradient field, where the first magnetic field changes slowly in time terms and with a high amplitude and the second magnetic field changes rapidly in time terms and with a low amplitude. Two magnetic fields which change at different rates and with different amplitudes are generated—preferably by two coil arrangements. A further advantage is that the field changes may be so fast (e.g. >20 kHz) that they are above the limit of human audibility. It may likewise be provided that the two magnetic fields run essentially perpendicular to one another in the examination area. This allows the movement of the field-free point in a two-dimensional area. An expansion to a three-dimensional area is obtained by virtue of a further magnetic field which has a component that runs perpendicular to the two magnetic fields. An arrangement having a filter connected downstream of the coil arrangement is likewise advantageous, said filter suppressing from the signal induced in the coil arrangement the signal components in a first frequency band and allowing through the signal components in a second frequency band which contains higher frequency components than the first frequency component. This makes use of the fact that the magnetization characteristic in the region in which the magnetization passes from the unsaturated state to the saturated state is non-linear. This non-linearity means that a magnetic field which runs for example in a sinusoidal manner over time with the frequency f in the range of non-linearity brings about a temporally changing induction with the frequency f (fundamental component) and integer multiples of the frequency f (upper or higher harmonics). The evaluation of the upper harmonics has the advantage that the fundamental component of the magnetic field that is active at the same time for moving the field-free point does not have any influence on the evaluation.

Suitable magnetic particles are those which can become saturated in the case of a sufficiently small magnetic field. A necessary prerequisite for this is that the magnetic particles have a minimum size or a minimum dipole moment.

Suitable magnetic particles advantageously have dimensions which are small compared to the size of the voxels, the magnetization of which is to be determined by means of the method according to the invention. Furthermore, the magnetization of the particles should preferably become saturated at field strengths of the magnetic field which are as low as possible. The lower the field strength necessary for this, the higher the spatial resolution capability and the weaker the (external) magnetic field that is to be generated in the examination area, in each case with the resolution remaining the same. Moreover, the magnetic particles should have a dipole moment that is as high as possible and a high saturation induction in order that the change in magnetization results in output signals that are as great as possible. When using the method for medical examinations, it is also important that the particles are non-toxic.

Advantageously, the magnetic particles have an anisotropy that is sufficient for the saturation magnetization of the particle to take place also by geometric (Brown's) rotation. Those magnetic particles in which the magnetization reversal takes place simultaneously both by means of geometric rotation and by means of Neel's rotation are particularly preferred. In this case, it has proven to be particularly advantageous if the internal anisotropic field is at least 0.1 mT or preferably at least 0.5 mT. According to a preferred refinement of the method according to the invention it is proposed that the magnetic particle is an anisotropic monodomain particle. Also a particle mixture can be used having isotropic and anisotropic particles.

Suitable magnetic monodomain particles are preferably dimensioned such that only a single magnetic domain (the monodomain) can form therein and a number of white regions are not present. According to a particularly preferred variant of the invention, suitable particle sizes lie in the range from 20 nm to around 800 nm, with the upper limit also depending on the material used. In respect of monodomain particles, use is preferably made of magnetite ($Fe_3O_4$), maghemite ($\gamma$-$Fe_2O_3$) and/or non-stoichiometric magnetic iron oxides.

In general it is advantageous if the monodomain particles have a high effective anisotropy. The term effective anisotropy is in this case to be understood as meaning the anisotropy resulting from the form anisotropy and the mean crystal anisotropy. In the aforementioned case, a change in the magnetization direction requires a rotation of the particles, that is to say that the magnetization reversal upon application of an external magnetic field takes place by means of Brown's rotation or geometric rotation.

According to an alternative embodiment of the method according to the invention it may be provided that the magnetic particle is a hard- or soft-magnetic, in particular a hard-magnetic, multidomain particle. These multidomain particles are usually relatively large magnetic particles in which it is possible for a number of magnetic domains to form. Such multidomain particles advantageously have a low saturation induction.

Hard-magnetic multidomain particles essentially have the same magnetic properties as monodomain particles having a high effective anisotropy. Soft-magnetic multidomain particles with a low saturation magnetization are particularly suitable if they have an asymmetric external shape.

Suitable hard-magnetic materials comprise, for example, Al—Ni, Al—Ni—Co and Fe—Co—V alloys and also barium ferrite (BaO 6×$Fe_2O_3$).

According to the invention it is provided that the magnetic particles become saturated upon application of an external magnetic field, in particular having a strength of about 100 mT or less. Of course, greater saturation field strengths are also suitable for the method according to the invention.

For many applications, suitable magnetic field strengths are even about 10 mT or less. This strength is sufficient even for many tissue or organ examinations. However, good measurement results can also be achieved with field strengths in the region of 1 mT or less or of around 0.1 mT or less. By way of example, concentration, temperature or pH can be determined with a high degree of accuracy and definition at magnetic field strengths of around 10 mT or less, of around 1 mT or less and at around 0.1 mT or less.

Within the context of the present invention, the term external magnetic field in which the magnetic particles become saturated or are saturated is to be understood as meaning a magnetic field in which around half the saturation magnetization is achieved.

One preferred refinement of the method according to the invention is characterized in that the material for the covering or coating of the magnetic particles used can be degraded or dissolved thermally, chemically, biochemically, by means of electromagnetic radiation or ultrasound and/or mechanically.

It may be provided that the material for the covering or coating comprises polysaccharides, starch, in particular dextrins or cyclodextrins, waxes, oils, fats, glycerin, gels or plastics, in particular thermoplastic polymers or blends thereof.

It may furthermore be provided that at least some of the magnetic particles have a coating or covering consisting of at least one protein, polypeptide, antibody and/or organosilane.

The coating of magnetic particles with biologically degradable materials, e.g. with dextrans and proteins, is described in DE 37 51 918 T2. Particle coatings comprising organic polymers are furthermore disclosed in Shen et al., J. Magn. Magn. Mater. 1999, 194, pages 37 ff. and in Del Gratta et al., Phys. Med. Biol. 1995, 40, pages 671 ff. The coating of magnetic particles can likewise be found in EP 186 616 A1.

Particularly suitable methods are characterized in that the evaluation takes place by means of the following steps:

a) selection of a path for the movement of the first part-area having a low magnetic field strength within the examination area, b) recording of reference data by means of reference samples along the path according to a) at at least one location, in particular a number of locations, in the case of at least two, in particular a number of, external parameters using at least a first receiving coil, c) interpolation and/or extrapolation of the reference data recorded in b) in respect of points and external parameters not recorded in step b), d) measurement of the path within the examination area in a sequence that is identical to that used for the recording of data by means of reference samples according to b) via at least a first and/or second receiving coil, and e) comparison of the data obtained according to d) with the reference data according to b) and/or c), in particular by minimizing the error square.

In this case, it is likewise advantageous if, in a step c') that follows step c), the reference data obtained in steps b) and/or c) are converted to the characteristics of at least a second receiving coil used for the measurement in step d).

A further development of the method is characterized in that in a further step f) the data obtained by means of comparison in step e) are assigned to a gray value for a pixel to give an image, with the relative pixel intensity representing the degree of the determined external parameters.

It may furthermore be provided that in a further step g) the images obtained in step f) are displayed in a merged image.

It is likewise possible that the sequence of steps d) and e) is repeated at least once.

A path is defined by the spatial change in the weak-field or field-free part-area of the gradient field through an examination area. It is consequently a so-called zero point path. A suitable path may be prescribed for example by two alternating magnetic fields having a different direction but the same frequency and may describe a circle. Alternatively, the ratio of the frequencies of these fields may be an integer multiple and lead to folded structures. A particularly dense sampling and hence also referencing of the examination area is achieved when the (zero point) path describes a Lissajous figure. The reference data determined at the respective positions in the examination area are determined in the case of at least two known external parameters, e.g. different temperatures or pH values, in the examination area and used for referencing. The reference sample characterizes a region in the examination area the magnetic state of which (e.g. particle type, concentration and distribution) is known. The referencing or calibration may be carried out both on the actual examination object and on an (in vitro) reference sample as long as the measurement conditions in the examination area can be reliably adjusted.

The recording of reference data may be omitted if the properties or the behavior of the magnetic particles in a referenced examination area are already sufficiently well known and all the necessary reference data can be calculated from a single registering of the magnetic behavior of the examination area.

The invention also relates to an apparatus to determine the spatially resolved determination of physical, chemical and/or biological properties or state variables and/or the change in physical, chemical and/or biological properties or state variables in an examination area of an examination object comprising:

a) means to generate a magnetic field with a spatial distribution of the magnetic field strength such that the area of examination consists of a first sub-area with lower magnetic field strength and a second sub-area with a higher magnetic field strength, b) means to change the spatial location of both sub-areas in the area of examination so that the magnetization of the particles changes locally, c) means for the acquisition of signals that depend on the magnetization in the area of examination influenced by this change, d) means for the evaluation of said signals to obtain information about the spatial distribution of the signals in the area of examination and e) means to perform calibration measurements preferably according to a method as described above, comprising means to record reference data on reference samples and means to compare the signals obtained in step c and/or d with the reference data to evaluate spatially resolved information about in situ, physical, chemical and/or biological properties or state variables in the area of examination.

The invention further relates to a functionalised magnetic particle composition for imaging physico-chemical parameters in the examination area with a magnetic particle imaging techniques, comprising magnetic particles coated with a functional coating material that changes physico-chemical properties when exposed to conditions prevailing in the examination area such that the mobility and/or rotational freedom of the magnetic particles in the examination area changes in a way and/or to an extent depending on the physico-chemical conditions. The term physico-chemical is to be construed very broadly and also includes for example biological, biochemical, microbiological, geologic, morphologic, genetic, process technical etc.

The underlying principle is that the magnetic particles that are restricted in mobility, in particular rotational mobility, respond differently to the imposed external magnetic field in the magnetic particle imaging technique than magnetic particles that are not restricted. The functional coating can be removed in the examination area to reduce the mobility restriction. Reversely, the functional coating can have the function to ensure that in the examination area a mobility restriction is created. The functional coating material on the magnetic particles is chosen in view of the specific physicochemical properties that are to be examined in the examination area. In parts of the examination area where the functional coating material reacts to the specific conditions in the examination area and mobility of the magnetic particles is changed, a contrast in the imaging technique can be developed compared to those parts of the examination area where there is less or no change. In that way the functional coating can be used to discriminate and image different physical chemical environments as will be described in the various embodiments of the functionalised magnetic particle compositions according to the invention.

In a preferred embodiment, the change in particular the at least part the removal of the particle coating results in an increased rotation freedom of the magnetic particle. In this case, before administering to the examination area the magnetic particle is hindered in geometrical rotation, whereas after the changing of the functional coating the magnetic particle as an increased freedom of geometric rotation. In view of that it is preferred that the magnetic particles are mono-domain particles having have an anisotropy, the magnetisation of which is reversed at least in part by geometric rotation. The functionalised magnetic particle composition preferably comprises magnetic particles that are monodomain particles having have an internal anisotropy field of at least 0.1 mT, preferably at least 0.5 mT and/or wherein the composition has an opening in the hysteresis loop in the magnetisation curve of at least 0.1 mT, preferably at least 0.5 mT. This opening of the hysteresis loop is present e.g. when most of the particles in the composition are aligned with their easy axis in the direction of the external field. It is also necessary that the hysteresis loop is measured fast enough to avoid geometric rotation of the particles.

Another embodiment of the functionalised magnetic particle composition is for the imaging of the temperature in the examination area, wherein the functional coating material has a viscosity that is dependent on the temperature within a temperature range of interest in the examination area. For the in vivo examination of living beings the temperature window of interest is between 30 and 50 degree centigrade. In this embodiment the magnetic particles have a higher rotational mobility and hence show an different response to the external magnetic fields at different temperature. In particular, in case the viscosity decreases with temperature, the high-temperature parts of the examination area will show an improved response to the external magnetic field.

In an alternative embodiment of the functionalised magnetic particle composition according to the invention for the imaging of temperature in the examination area the functional coating is a material having a melting temperature in a temperature window of interest in the examination area. More preferred, the particle composition comprises a mixture of at least two different parts having a different functional coating with a different melting temperature. In this embodiment the magnetic particles regain a higher rotational mobility when the temperature in the examination area rises above the melting temperature of the functional coating and the viscosity of the coating reduces sharply.

This technique allows a very accurate measurement of the temperature in the examination area. In principle, temperature differences can be measured with an accuracy up to about 0.1 degree centigrade. Depending on the particular object of examination the composition of the functional magnetic particle composition is chosen such as to cover a particular temperature range of interest. Temperature differences within a range of five or even within two or one degree centigrade can be visualised with the imaging technique using the functional magnetic particle composition according to the invention. It is preferred that before the actual measurement a calibration is performed to correlate the signal obtained in the imaging technique with known temperatures.

For investigation of the temperature in living organisms the melting temperature of the one or more different functional coating materials is preferably chosen between 30 and 50° C. Suitable coating materials for this purpose are example paraffins, sugars or low molecular weight aliphatic carboxylic acids. Differences in melting temperature can be created by taking various different pure compounds were by taking mixtures of two or more different compounds in different proportions. For example, the range of different melting temperatures can be created by mixing two different molecular weight paraffins in different proportions.

In another embodiment there is provided a functionalised magnetic particle composition for the imaging of pH in the examination area, wherein the functional coating comprises a material that dissolves or degrades at a rate depending on the pH of the surrounding medium in the examination area. Various different functional coating materials can be envisaged for this purpose. For example, the functional coating comprises a hydrolysable coating material, for example an amino acid, that hydrolyses in an aqueous medium at a rate dependent on the pH of the aqueous medium.

In yet another embodiment there is provided a functionalised magnetic particle composition wherein the magnetic particles are coated with a material comprising a functional group reactive to a specific target molecule in the examination area wherein the magnetic particles after binding to the target molecule have a reduced mobility, in particular a reduced rotation mobility, such as to produce contrasts in the magnetic particle image between the area as that do and do not contain the specified target molecule. This opens up a wide range of possible applications in clinical diagnosis and therapy. In this embodiment, the mobility, in particular the rotational mobility, of the magnetic particles are restricted after the functional group of the magnetic particle binds to the target molecule in the examination area, thus creating a contrast this those parts of the examination area where the magnetic particles are not bonded to said target molecule.

The functional group can for example be a specific amino acid and the target molecule an enzyme. In another embodiment the functional group is a DNA or RNA strand or sequence complementary and/or capable of binding with a target DNA or RNA. In yet another embodiment the target molecule is an antibody.

In another embodiment of the invention a functionalised magnetic particle composition is provided for the examination of enzyme activity in the examination area, wherein the magnetic particles are coated with a material, in particular a protein, that is enzymatically decomposed by the target enzyme.

In general the magnetic particles in the magnetic particle administering composition, are chosen such that good magnetic particle images, in particular a good resolution can be obtained in a given field gradient. In unpublished German patent application number 101 51778.5 a magnetic particle imaging method is described. It is generally described that magnetic mono-domain particles having a size between 20 and 800 nanometers or a glass beat coated with a magnetic coating can be used in this method. However, in order to achieve a good magnetic imaging contrast and resolution at relatively low magnetic field gradients, improved magnetic particle compositions are highly desirable. The inventors have found magnetic particles having improved magnetic particle imaging properties.

Preferably, the magnetic particles in the magnetic particle administering composition have a magnetization curve having a step change, the step change being characterized in that the magnetization change, as measured in an aqueous suspension, in a first field strength window of magnitude delta around the inflection point of said step change is at least a factor 3 higher than the magnetization change in the field strength windows of magnitude delta below and/or in the field strength windows of magnitude delta above the first field strength window, wherein delta is less than 2000 microtesla, preferably less than 1000 microtesla, and wherein the time in which the magnetisation step change is completed in the first delta window is less than 0.01 seconds, preferably less than 0.005 sec, more preferably less than 0.001, most preferably less than 0.0005 seconds. It has been found, that such magnetic particles are particularly suitable for magnetic particle imaging, in particular for obtaining a good resolution of the image. It is further preferred, that the magnetic particle composition has a magnetisation curve, wherein the step change is at least 10%, preferably at least 20%, more preferably at least 30% and most preferably at least 50% of the total magnetisation of the particle composition as measured at an external magnetisation field of 1 Tesla. It is further preferred, that the magnetization change in the first field strength window of magnitude delta around the inflection point of said step change is at least a factor 4, preferably at least a factor 5 higher than the magnetization change in the field strength windows of magnitude delta below or in the field strength windows of magnitude delta above the first field strength window.

The magnetic particle composition is particularly useful for use in a magnetic particle imaging technique. The particles show good spatial resolution at relatively low field strength gradients. Further, the magnetic particle composition allows for a relatively high scanning speed for examining a large examination area. For example, for application in medical magnetic particle imaging, where the step change occurs preferably at a delta value below 1000 microTesla, the particle composition has a resolution value better than between 0.1 and 10 mm at magnetic field strength gradients between 10 and 0.1 T/m. With the magnetic particle imaging technique using the magnetic particle compositions according to the invention extremely good resolution can be obtained, for example in a range from 0.1 to 10 micrometers in applications, where are very high magnetic field is gradients can be achieved, for example in microscopy. It is noted that strictly speaking, magnetic field strength is expressed in H (A/m). However, in the present application, when reference is made to magnetic field strength, B-fields are meant. A magnetic fields B of 2000 µT as described above corresponds to an H field of 2 mT/µ0=1.6 kA/m, that is the equivalent H field that would produce a B field of 2 mT in vacuum.

Preferably, the functionalised magnetic particle compositions according to the invention and the method according to the invention as described above comprise magnetic particles that meet the specified step change requirements of the magnetic particle composition according to the invention as described above.

A method for measuring the magnetisation curve and the required step change is as follows. A sample of a magnetic particle composition is suspended in water, optionally with the help of a simple detergent. To prevent clumping and/or to de-agglomerate the magnetic particles an ultrasound treatment possible can be used. The concentration of the magnetic particle composition is less than 0.01 gr core mass per liter of solvent. With core mass is meant the mass of the magnetic material in the magnetic particle composition. The suspension is brought into a fast magnetometer. (i.e. a device that measures the magnetization of the sample while an external field is applied). Suitable fast magnetometers are known to the expert. The magnetometer is equipped with means allowing to produce an external field at the sample position in at least two orthogonal directions simultaneously, i.e. to produce any magnetic field below a given maximum amplitude and a given maximum speed of change. The magnetisation is measured also in at least two orthogonal directions in the same plane.

First the saturation magnetisation is measured. For this, a magnetic field of about one Tesla is applied in one direction and the magnitude of magnetization is measured after at least 10 seconds. Then the measurement sequences for determining the step change starts. The sequence starts with choosing a field vector with an external field magnitude below 20 mT. This field is applied for at most 100 seconds. Then a second direction is chosen. This direction defines the scalar values of the field H and the magnetization M. The field is rapidly changed, preferably less than 1 millisecond, so that it lies now in –H direction with some magnitude below 20 mT. Then the field is changed from –H to +H e.g. in a linear way and the (now scalar i.e. projected) magnetization is recorded. The magnetization curve is recorded in less than 0.01 s but longer than 1 µs. Where the magnetisation curve shows a step change, a first window of size delta is positioned centrally on the inflection point of the magnetisation step change. Similarly, a window of size delta is positioned below and above the first window, and the required step change is evaluated by determining the change in magnetisation in each of the windows.

Whether or not a given magnetic particle composition has the required step change depends in a complicated way on many variables, for example of the size of the particles, the particle size distribution, the shape of the particles, the damping constant for Neel rotation, the type of magnetic material, the crystallinity and the stochiometry of the composition of the magnetic material. It has been found that it is particularly important that the particle size distribution of the particle composition is narrow. Preferably, the magnetic particle composition according to the invention has a narrow particle size distribution wherein at least 50 weight % of the particles have a particle size between plus or minus 50%, preferably 25%, more preferably 10% of the average particle size. Preferably, the amount of particles within the specified windows, is at least 70 wt %, preferably at least 80 wt %, and most preferably at least 90 wt %. Particularly good results are obtained with mono-domain particles have a low magnetic anisotropy with a field needed for inducing Neel rotation of substantially below 10 mT, preferably below 5 mT, more preferably below 2 mT. Preferably, the magnetic particles are mono-domain particles having an average particle size between 20 and 80 nanometers, more preferably between 25 and 70 nanometers, must preferably between 30 and 60 nanometers, wherein at least 50, preferably at least 60, more preferably at least 70 weight % of the particles have a particle size between the average particle size plus or minus 10 nanometer.

In an alternative embodiment of the magnetic particle composition according to the invention, the magnetic particle is a multi-domain particle having substantially a needle shape having a demagnetisation factor of less than 0.001. This magnetic particle composition is particularly useful in non-medical applications where the needles shape is not a disadvantage. In another alternative embodiment, the magnetic particle composition according to the invention comprises magnetic particles comprising a non-magnetic core covered with a magnetic coating material, wherein the thickness of the coating is between 5 and 80 nanometers and wherein the demagnetisation factor is less than 0.01 and a diameter below 3001 µm. Also in these alternative embodiments it is advantageous to have a small particle size distribution as described above. The physical parameters of the magnetic particles in these embodiments are preferably chosen to meet the step change requirement as described above for achieving good imaging properties.

The magnetic particle composition according to the invention can be manufactured by first forming magnetic particles, for example by precipitation, for example by contacting a solution comprising ferrous and ferric ions with a solution comprising sodium hydroxide as described above. In principle, a known precipitation process can be used. It is also possible to grind the particles from bulk material, for example using a high speed ball mill. The essential next step for obtaining a good magnetic particle composition is the selection and separation of the particles. The first step is to perform a size selection process by filtering and/or centrifuge methods. The next step is to perform a selection process based on the magnetic properties of the particles, for example, using oscillating magnetic gradient fields.

The present invention is based on the surprising knowledge that the time constant for Brown's, i.e. geometric, rotation of magnetic particles in an examination area can be determined very precisely and also in a locally delimited manner, as a result of which it is possible to obtain information about the physical, chemical and/or biological parameters in the examination area in a manner that is simple in terms of apparatus and reliable. For this it is sufficient to introduce into the examination area magnetic particles that have been coated beforehand and to monitor how the coating or covering of the magnetic particle is degraded or dissolved and/or in the case of which influencing variables this covering or coating is degraded or dissolved. Furthermore, it is possible to ascertain whether and under which conditions coatings or coverings swell or increase in size and thus change the mobility of the encompassed magnetic particle. It is moreover advantageous that the examination of the mobility of the magnetic particles in the examination area can take place in real time. Finally, it is an advantage of the method according to the invention that physical, chemical and/or biological information about the examination area or parts thereof can be obtained with a high spatial resolution. This relates to the examination of both biological and non-biological objects.

The features of the invention that are disclosed in the above description and in the claims may be essential for the implementation of the invention in its various embodiments both individually and in any desired combination.

The invention claimed is:

1. A method for the spatially resolved determination of physical, chemical and/or biological properties or state variables, particularly substance concentrations, temperature, pH and/or physical fields, and/or the change in such physical, chemical and/or biological properties or state variables in an examination area of an examination object by determining a change in spatial distribution and/or mobility of magnetic particles in the examination area or in parts thereof as a function of the effect of physical, chemical and/or biological influencing variables on at least a part-area and/or in the physical, chemical and/or biological conditions in at least a part-area of the examination area, the method comprising:

a) introducing coated magnetic particles having a coating into at least part of the examination area,
b) generating a magnetic field with a spatial profile of the magnetic field strength such that there is produced in the examination area a first part-area having a low magnetic field strength and a second part-area having a higher magnetic field strength,
c) changing the relative spatial position of the first and second part-areas in the examination area or changing the magnetic field strength in the first part-area so that the magnetization of the particles is locally changed,
d) detecting signals that depend on magnetization in the examination area that is influenced by said changing, and
e) evaluating the signals so as to obtain information about change in the spatial distribution and/or mobility of the magnetic particles in the examination area, wherein the coating is degradable and inhibits mobility of the particles.

2. A method as claimed in claim 1, wherein said changing takes place before said introducing, or said introducing and said changing are carried out essentially at the same time, and/or said changing, said detecting and said evaluating are repeated at least once.

3. A method as claimed in claim 1, wherein the examination object is a polymer material, a polymer melt, a microorganism, a plant, a plant part, a living thing or a part of a living thing.

4. A method as claimed in claim 3, wherein the polymer is a thermoplastic polymer or a polymer blend.

5. A method as claimed in claim 1, wherein a degree of mobility of the magnetic particles in the examination area is determined continuously or at intervals and is correlated with a state variable or property of the examination area, the state variable including a temperature, a concentration and/or a viscosity.

6. A method as claimed in claim 1, wherein a degree of mobility of the magnetic particles in a polymer melt that is forming or curing is determined continuously or at intervals and is correlated with a degree of curing or a degree of melting of a polymer material.

7. A method as claimed in claim 6, wherein the polymer material is a thermoplastic polymer.

8. A method as claimed in claim 1, wherein at least some of the magnetic particles have anisotropic properties.

9. A method as claimed in claim 1, wherein an effective anisotropy of the magnetic particles is great enough for a reversal of the magnetization of the magnetic particles to take place by geometric (Brown's) rotation and by Neel's rotation.

10. A method as claimed in claim 1, wherein the magnetic particles are monodomain particles, the magnetization of the monodomain particles is reversed by Brown's rotation and Neel's rotation.

11. A method as claimed in claim 1, wherein the magnetic particle is a hard-magnetic or soft-magnetic multidomain particle.

12. A method as claimed in claim 1, wherein the magnetic particles comprise hard-magnetic materials.

13. A method as claimed in claim 12, wherein the hard-magnetic materials comprise Al—Ni, Al—Ni—Co and Fe—Co—V alloys and also barium ferrite (BaO 6x$Fe_2O_3$).

14. A method as claimed in claim 1, wherein the coating is degradable thermally, chemically, biochemically, by electromagnetic radiation or ultrasound and/or mechanically.

15. A method as claimed in claim 1, wherein the coating comprises polysaccharides, starch, waxes, oils, fats, glycerin, gels or plastics including thermoplastic polymers or blends thereof.

16. A method as claimed in claim 15, wherein the starch is a dextrin or a cyclodextrin.

17. A method as claimed in claim 1, wherein the coating of at least some of the magnetic particles consist of at least one protein, polypeptide, antibody and/or organosilane.

18. A method as claimed in claim 1, wherein said evaluating comprises:
a) selection of a path for movement of the first part-area having a low magnetic field strength within the examination area,
b) recording of reference data by reference samples along the path according to said selection at least one location in the case of at least two external parameters using at least a first receiving coil,
c) interpolation and/or extrapolation of the reference data recorded during said recording to points and for external parameters not recorded during said recording,
d) measurement of the path within the examination area in a sequence that is identical to that used during said recording by reference samples according to said recording via the at least first receiving coil, and
e) comparison of data obtained during said measurement with the reference data obtained during said recording and/or during said interpolation by minimizing the error square.

19. A method as claimed in claim 18, wherein after said interpolation, the reference data obtained during said recording and/or during said interpolation are converted to characteristics of at least a second receiving coil used during said measurement.

20. A method as claimed in claim 18, wherein data obtained during said comparison are assigned to a gray value for a pixel to provide images, with relative pixel intensity representing a degree of the determined external parameters.

21. A method as claimed in claim 20, wherein the images obtained are displayed in a merged image.

22. A method as claimed in claim 18, wherein a sequence of said measurement and said comparison is repeated at least once.

23. A method for the spatially resolved determination of physical, chemical and/or biological properties or state variables, particularly substance concentrations, temperature, pH and/or physical fields, and/or the change in such physical, chemical and/or biological properties or state variables in an examination area of an examination object by determining a change in spatial distribution and/or mobility of magnetic particles in the examination area or in parts thereof as a function of the effect of physical, chemical and/or biological influencing variables on at least a part-area and/or in the physical, chemical and/or biological conditions in at least a part-area of the examination area, the method comprising:
a) introducing at least partially coated magnetic particles having a partial coating into at least part of the examination area,
b) generating a magnetic field with a spatial profile of the magnetic field strength such that there is produced in the examination area a first part-area having a low magnetic field strength and a second part-area having a higher magnetic field strength,
c) changing the relative spatial position of the first and second part-areas in the examination area or changing the magnetic field strength in the first part-area so that the magnetization of the particles is locally changed,
d) detecting signals that depend on magnetization in the examination area that is influenced by said changing, and
e) evaluating the signals so as to obtain information about change in the spatial distribution and/or mobility of the magnetic particles in the examination area, wherein the partial coating is degradable and inhibits mobility of the particles.

24. A method for the spatially resolved determination of physical, chemical and/or biological properties or state variables, particularly substance concentrations, temperature, pH and/or physical fields, and/or the change in such physical, chemical and/or biological properties or state variables in an examination area of an examination object by determining a change in spatial distribution and/or mobility of magnetic particles in the examination area or in parts thereof as a function of the effect of physical, chemical and/or biological influencing variables on at least a part-area and/or in the physical, chemical and/or biological conditions in at least a part-area of the examination area, the method comprising:

a) introducing magnetic particles into at least part of the examination area and coating at least some of the particles in the examination area with a coating,
b) generating a magnetic field with a spatial profile of the magnetic field strength such that there is produced in the examination area a first part-area having a low magnetic field strength and a second part-area having a higher magnetic field strength,
c) changing the relative spatial position of the first and second part-areas in the examination area or changing the magnetic field strength in the first part-area so that the magnetization of the particles is locally changed,
d) detecting signals that depend on magnetization in the examination area that is influenced by said changing, and
e) evaluating the signals so as to obtain information about change in the spatial distribution and/or mobility of the magnetic particles in the examination area, wherein the coating is degradable and inhibits mobility of the particles.

* * * * *